United States Patent [19]

Drewlow

[11] Patent Number: Plant 6,115

[45] Date of Patent: Feb. 23, 1988

[54] POINSETTIA PLANT NAMED MINSTREL

[75] Inventor: Lyndon W. Drewlow, Ashtabula, Ohio

[73] Assignee: Mikkelsens Inc., Ashtabula, Ohio

[21] Appl. No.: 824,795

[22] Filed: Jan. 31, 1986

[51] Int. Cl.[4] ..... A01H 5/00

[52] U.S. Cl. ..... Plt./86

[58] Field of Search ..... Plt./86

*Primary Examiner*—Robert E. Bagwill

*Attorney, Agent, or Firm*—Schwartz, Jeffery, Schwaab, Mack, Blumenthal & Evans

[57] ABSTRACT

A poinsettia plant named Minstrel particularly characterized by the combined characteristics of bright red colored bracts, dark green foliage, vigorous dwarf growth habit, early flowering, and by its ability to be grown as a single stem or pinched plant.

1 Drawing Figure

The present invention relates to a new and distinctive cultivar of poinsettia plant known by the cultivar name Minstrel, and botanically known as *Euphorbia pulcherrima.*

Minstrel was developed by me through controlled breeding by crossing Mikkelsen Seedling No. 80-70-2 (seed parent)×Mikkelsen Seedling No. 80-189-1 (pollen parent). Minstrel was given the breeding number 83-523-2.

Minstrel has been asexually reproduced by me by cuttings in the greenhouses of Mikkelsens Inc., Ashtabula, Ohio, and has been found to retain its distinctive characteristics through successive propagations.

The following characteristics distinguish the new cultivar from its parents and from other poinsettias commercially known and used in the floriculture industry:

1. The bract color of Minstrel is a brighter red than Merrimaker (disclosed in pending U.S. Plant patent application of James C. Mikkelsen, filed Jan. 14, 1986), and a more intense, deeper red than Paul Mikkelsen (disclosed in U.S. Plant Pat. No. 2,328), the patented cultivars Hegg Brilliant and Gottbiers V14 Glory, and the unpatented cultivar Super Rochford.

2. Minstrel has shorter internodes than Gottbiers and is more compact when grown under similar conditions.

3. The involucre has a similar number of bracts as Paul Mikkelsen, Hegg Brilliant, Super Rochford and Gottbiers, but not as many as Merrimaker. The diameter of Minstrel is smaller than all of the mentioned cultivars due to the genetic dwarf nature of the plant.

4. Minstrel has foliage color similar to Gottbiers V14 Glory but not as dark green as Merrimaker, Hegg Brilliant and Rochford types. The leaf is shorter and broader than Glory, but both have deep cuts in some leaves.

5. Flower clusters (cyathia) remain tight and do not split open as does Paul Mikkelsen, and the Hegg and Rochford cultivars. Glory has a smaller, more compact cyathia cluster.

6. The bract is ovate in shape, which is similar to Hegg and Rochford types. Merrimaker is more oval and Glory is more pointed.

7. Cyathias are retained slightly longer than the Heggs and Rochford types, but not as long as Merrimaker. Minstrel will tolerate some moisture, temperature and nutrient stress without dropping the cyathia.

8. Minstrel is similar to Glory, Heggs and Rochford in breaking with new shoots after removal of the terminal meristem. Stems are not grassy when compared with the above cultivars, and the stem caliber is superior, but not as large as Merrimaker.

9. Rooting time is similar to Paul Mikkelsen, Heggs and Rochfords, being well rooted in 14 to 16 days at 21° C., thereby being superior to Glory which takes longer to root and does not root as uniformly.

10. Under natural short days in Ohio, Minstrel developed bracts and shed pollen three weeks earlier than Glory, Heggs or Rochfords. Under controlled day length using black-out cloth all cultivars flowered nearly the same indicating that Minstrel initiates flowers on a longer critical natural day length.

The accompanying colored photographic drawing, taken as a top view, illustrates the overall appearance of the new cultivar, with the colors being as true as possible to obtain in color reproductions of this type.

The following is a detailed description of the new cultivar based on plants produced under commercial practices in the greenhouses of Mikkelsens Inc., Ashtabula, Ohio, and photographed in December flowering. Color references are made to The Royal Horticultural Society Colour Chart except where general terms of ordinary dictionary significance are used.

Parentage: Controlled breeding by crossing Mikkelsen Seedling No. 80-70-2 (seed parent)×Mikkelsen Seedling No. 80-189-1 (pollen parent).

Propagation:

(A) *Type cutting.*—Stems, 50 to 66 mm.

(B) *Time to root.*—14 to 16 days, 12 to 14 hour day length at 21° C. summer; 16 to 18 days, 12 to 14 hour day length at 21° C. winter.

(C) *Rooting habit.*—Coarse, fibrous, numerous.

Plant description:

(A) *Form.*—Upright; non-self branching but breaks well from a pinch (removal of growing point); compact, true genetic dwarf.

(B) *Growth habit.*—Compact but vigorous with short internodes even under high temperatures; heavy stems hold bracts well.

(C) *Foliage.*—Petioles are reddish-purple with pinking of the midrib of most leaves increasing as the bracts are approached; numerous and close due to short internodes; leaves alternate. (1) Size: Petiole 35 to 40 mm. on mature basal leaves to 15 to 20 mm. below bracts; basal leaves 12 to 13 cm. long, 10 to 11 cm. wide; leaves near bract 6 to 7 cm. long, 5 to 6 cm. wide. (2) Shape: Oakleaf with acuminate leaf apices and rounded leaf base. (3) Texture: Upper side glabrous, veins slightly recessed; under side rough, veins protruding. (4) Margin: Deeply lobed with the sinuses v-shaped in most cases. (5) Color: Young foliage top side between 146B and 146C; under side 146C. Mature foliage top side 137B; under side 146B.

Flowering description:

(A) *Flowering habits.*—Minstrel flowers earlier than most commercial cultivars, apparently having a longer critical day length for flower initiation. Under controlled day length, development time is approximately 10 weeks. Minstrel is the first bright red genetic dwarf designed for 10 cm. and 6 cm. plug production as flowering plants. The dwarf type plant can be produced without the use of growth regulators or other means of restructing growth. There will have to be considerable research into the matter of flower initiation under natural day lengths coupled with temperatures in comparison to controlled day length prior to initiation and at initiation. It is very apparent that Minstrel is flowering earlier than most commercial cultivars under natural day length in Ashtabula, Ohio but takes approximately the same time to develop when tested under exact controlled day lengths with other commercial cultivars. This characteristic of earlier flower initiation is of commercial significance.

(B) *Natural flowering season.*—The natural flowering season is mid to late November. Flowering time under controlled short days below 25° C. in summer is 10 weeks and in winter is 10 weeks. The cyathia will continue to develop and initiate until day length is greater than 13 hours and temperatures are no higher than 25° C.

(C) *Cyathia.*—Cyathia is average in size and does not grow apart (split) as the bract ages. The cyathia will continue to develop for several months. Rounded shape and medium size. Color of bud and stem is 146D with reddish tip on bud.

(D) *Borne.*—Continuously for several months with many cyathias per stem in regular clusters in varying stages of development. Cyathias borne on short, light green sturdy stems. Involucre is almost flat with only slight reflexing.

(E) *Quantity.*—Average for a poinsettia and highly dependent on cultural practices. Number will vary from 10 to 25 or more. Average retention when plants are subjected to light, temperature and moisture stresses.

(F) *Bracts.*—The last true leaves tend to become red. The primary bracts are 9 to 10 cm. long and 4 to 5 cm. wide with petioles 1 to 1.5 cm. long and ovate in shape. The secondary bracts are 6 to 7 cm. long and 3 to 3.5 cm. wide with petioles 0.5 to 1 cm. long as measured on a pinched plant. Bracts will be large on a single stem plant. Bract size will vary depending upon temperature, light, nutrition and other cultural practices. The bract head diameter is 20 to 25 cm. on a pinched plant, and 25 or more bracts are produced on a well grown plant. Color: Young bracts, top side, bright 45A; under side deeper than 45C; mature bracts top side brighter than 46B; under side 45C.

(G) *Reproductive organs.*—(1) Stamens: Numerous; anther oblong and reddish in color; filament red; pollen yellow. (2) Pistels: Stigma forked, reddish-purple; styles whitish green; ovaries, 3 celled and yellow-green in color. One nectar cup per cyathia; yellow in color; nectar abundant on mature cyathia.

Disease resistance: Bracts show resistance to botrytis. White fly has an apparent low preference to Minstrel as adjacent infested cultivars did not cause buildup of egg masses on Minstrel.

I claim:

1. A new and distinct cultivar of poinsettia plant named Minstrel, as illustrated and described, and particularly characterized by its bright red colored bracts; dark green foliage; vigorous, dwarf growth habit; early flowering; and by its ability to be grown as a single stem or pinched plant.

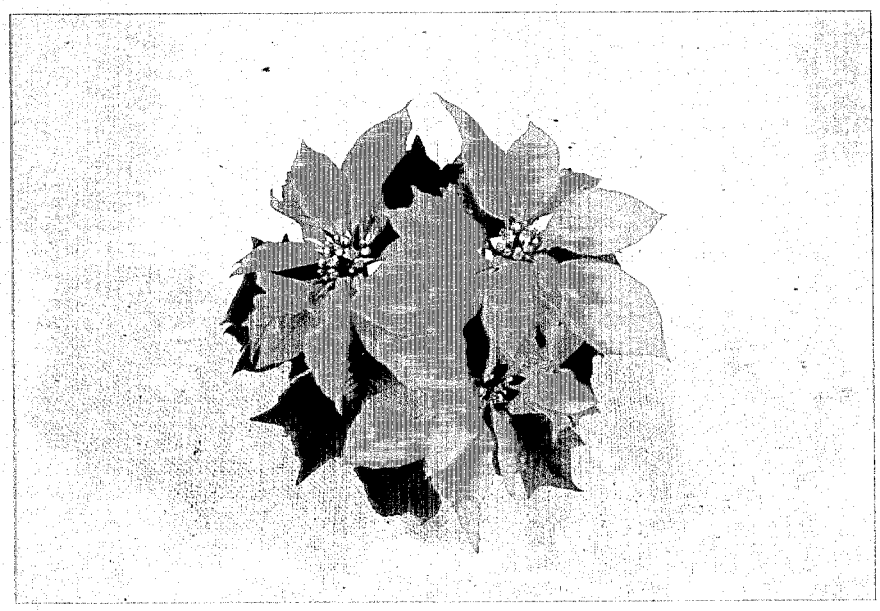

* * * * *